US009420981B2

(12) United States Patent
Baek et al.

(10) Patent No.: US 9,420,981 B2
(45) Date of Patent: Aug. 23, 2016

(54) COLLIMATOR AND INSPECTING SYSTEM USING THE SAME

(71) Applicant: UNIVERSITY-INDUSTRY FOUNDATION (UIF), Seoul (KR)

(72) Inventors: Jong Duk Baek, Incheon (KR); Chang Woo Lee, Yongin-si (KR)

(73) Assignee: UNIVERSITY-INDUSTRY FOUNDATION (UIF) (KR)

( * ) Notice: Subject to any disclaimer, the term of this patent is extended or adjusted under 35 U.S.C. 154(b) by 106 days.

(21) Appl. No.: 14/258,517

(22) Filed: Apr. 22, 2014

(65) Prior Publication Data

US 2015/0036787 A1    Feb. 5, 2015

(30) Foreign Application Priority Data

Aug. 5, 2013   (KR) .......................... 10-2013-0092624

(51) Int. Cl.
| | |
|---|---|
| *A61B 6/00* | (2006.01) |
| *A61B 6/06* | (2006.01) |
| *G21K 1/04* | (2006.01) |
| *A61B 6/03* | (2006.01) |
| *A61B 6/10* | (2006.01) |
| *G21K 1/02* | (2006.01) |
| *H05G 1/00* | (2006.01) |

(52) U.S. Cl.
CPC . *A61B 6/06* (2013.01); *A61B 6/032* (2013.01); *A61B 6/035* (2013.01); *A61B 6/107* (2013.01); *A61B 6/542* (2013.01); *G21K 1/02* (2013.01); *G21K 1/046* (2013.01); *H05G 1/00* (2013.01)

(58) Field of Classification Search
CPC .......... A61B 6/032; A61B 6/035; A61B 6/06; A61B 6/107; A61B 6/542; A61B 6/027; A61B 6/14; A61B 6/4233; A61B 6/037; G21K 1/02; G21K 1/04; G21K 1/025; G21K 1/046; G21K 1/10; G21K 5/04; G21K 1/043; G21K 1/06; G21K 1/067; G21K 2201/064; G21K 1/062; G21K 1/093
USPC .................................................. 378/147–153
See application file for complete search history.

(56) References Cited

U.S. PATENT DOCUMENTS

| | | | | |
|---|---|---|---|---|
| 4,126,786 | A | * | 11/1978 | LeMay .................. A61B 6/032 378/10 |
| 5,493,599 | A | * | 2/1996 | Mattson ................. A61B 6/032 378/147 |

(Continued)

FOREIGN PATENT DOCUMENTS

| | | |
|---|---|---|
| EP | 2446821 | 5/2012 |
| JP | 2005532109 | 10/2005 |

(Continued)

OTHER PUBLICATIONS

Korean NOA dated Jul. 14, 2014, issued in corresponding Korean Application No. 10-2013-0092624.

*Primary Examiner* — Thomas R Artman
(74) *Attorney, Agent, or Firm* — Onello & Mello, LLP.

(57) ABSTRACT

Disclosed are a collimator and an inspecting system using the same. According to an aspect of the present invention, there is provided a collimator for setting a radiation irradiation range, the collimator comprising: a shielding portion blocking the radiation; and a block portion comprising a plurality of unit pieces which can be opened or closed to selectively transmit the radiation.

3 Claims, 13 Drawing Sheets

(56) References Cited

U.S. PATENT DOCUMENTS

| | | | |
|---|---|---|---|
| 5,644,614 A | 7/1997 | Toth et al. | |
| 6,819,743 B2 * | 11/2004 | Kato | A61N 5/1042 378/147 |
| 6,850,596 B2 * | 2/2005 | Sundermann | A61B 6/583 378/147 |
| 6,968,036 B2 | 11/2005 | Carlsson et al. | |
| 7,336,758 B2 | 2/2008 | Seto et al. | |
| 8,184,775 B1 | 5/2012 | Fan et al. | |
| 2004/0136495 A1 | 7/2004 | Carlsson et al. | |
| 2011/0228898 A1 * | 9/2011 | Pelc | A61B 6/032 378/9 |
| 2012/0039446 A1 | 2/2012 | Cui et al. | |
| 2012/0069954 A1 | 3/2012 | Iso et al. | |
| 2012/0106695 A1 | 5/2012 | Fan et al. | |
| 2012/0170709 A1 | 7/2012 | Fan et al. | |
| 2013/0034200 A1 | 2/2013 | Hsieh et al. | |
| 2015/0016587 A1 * | 1/2015 | Baek | G01N 23/046 378/10 |

FOREIGN PATENT DOCUMENTS

| | | |
|---|---|---|
| JP | 2012086006 | 5/2012 |
| KR | 10-2006-0050407 | 5/2006 |
| KR | 2006214908 | 8/2006 |
| KR | 10-0697397 | 3/2007 |
| KR | 10-1076319 | 10/2011 |
| KR | 101076319 | 10/2011 |

* cited by examiner (a)

(b)

COLLIMATOR AND INSPECTING SYSTEM USING THE SAME

RELATED APPLICATIONS

This application claims priority from Korean Patent Application No. 10-2013-0092624 entitled COLLIMATOR AND INSPECTING SYSTEM USING THE SAME, filed on Aug. 5, 2013 in the Korean Intellectual Property Office, the disclosure of which is incorporated herein by reference in its entirety.

BACKGROUND OF THE INVENTION

1. Field of the Invention

The present invention relates to a collimator and an inspecting system using the same, and more particularly, to a collimator which can realize an ultra-low-dose radiation inspecting system by reducing the number of projection views without adjusting the power of a radiation source by adjusting an area that is to be irradiated with radiation and an inspecting system using the collimator.

2. Description of the Related Art

Medical devices that take an image of a body part of a patient by using radiation having penetrating nature are being widely used. However, such medical devices adversely affect patients due to a large amount of radiation exposure. For example, radiation can cause DNA changes, cancer, nausea, headaches, etc. depending on the radiation dose. Therefore, a collimator is used to reduce the amount of radiation exposure.

FIG. 1 is a diagram illustrating a conventional radiographic device.

Referring to FIG. 1, the conventional radiographic device includes a collimator 5 between a radiation source 3 which irradiates radiation and a sensor 4 which senses the radiation. The radiation may be incident on an object through the collimator 5. Here, an area to be irradiated with the radiation is adjusted by the collimator 5. Radiation that fails to pass through a gap of the collimator 5 is absorbed by blades made of a high band-gap material. That is, radiation adjusted by the collimator 5 is incident on an object, and the radiation that passes through the object is sensed by the sensor 4. The detected signal is processed by a processor and generated as an image.

In the conventional radiographic device, however, the collimator 5 can only adjust the beam width of radiation in order to limit a field of view (FOV).

Among radiographic devices, computed tomography (CT) technology has been continuously developed with an am to reduce the time required to obtain an image. In particular, the enhancement of the rotation speed of a CT gantry and the application of a multi-slice detector have greatly contributed to a reduction in the time required to obtain an image. However, the enhancement of the rotation speed of the CT gantry has reached the limit due to the weight of the gantry, and an increase in the number of multi-slice detectors generates a cone beam artifact.

Recently, the safety of CT imaging has been questioned due to radiation exposure. Therefore, research is being actively conducted to reduce the amount of radiation to which a patient is exposed. Some examples include a research on a low-dose CT system using tube current and a research on an image reconstruction system based on a compressive sensing theory. However, these researches have problems such as the degradation of projection data quality due to noise and the fast adjustment of the power of x-rays, respectively.

The present invention is focused on an image reconstruction system based on the compressive sensing theory among many researches on ultra-low-dose CT systems. A lot of research results have already showed that satisfactory image reconstruction is possible in a low-dose environment based on the compressive sensing theory even if a small number of projection views are used. In this case, however, the power of an x-ray source should be turned ON or OFF. Considering that the x-ray source rotates once per approximately 0.3 seconds in the case of diagnostic CT, there remains a technical challenge of adjusting the power of the x-ray source faster than the rotation speed of a high-speed gantry.

SUMMARY OF THE INVENTION

Aspects of the present invention provide a collimator which can reduce the number of projection views without adjusting the power of a radiation irradiator by freely adjusting an area that is to be irradiated with radiation and an inspecting system using the collimator.

However, aspects of the present invention are not restricted to the one set forth herein. The above and other aspects of the present invention will become more apparent to one of ordinary skill in the art to which the present invention pertains by referencing the detailed description of the present invention given below.

According to an aspect of the present invention, there is provided a collimator for setting a radiation irradiation range, the collimator comprising: a shielding portion blocking the radiation; and a block portion comprising a plurality of unit pieces which can be opened or closed to selectively transmit the radiation.

According to another aspect of the present invention, there is provided an inspecting system using a collimator, the inspecting system comprising: a radiation source which is located outside the collimator and irradiates radiation toward the collimator as the radiation source rotates; a detector which is located inside the collimator and detects radiation that transmits through the collimator as the detector rotates; and the ring-shaped collimator which selectively transmits radiation irradiated from the radiation source toward the detector.

The above and other features and advantages of the present invention will become more apparent by describing in detail exemplary embodiments thereof with reference to the attached drawings in which:

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE INVENTION

The present invention will now be described more fully hereinafter with reference to the accompanying drawings, in which preferred embodiments of the invention are shown. This invention may, however, be embodied in different fauns and should not be construed as limited to the embodiments set forth herein. Rather, these embodiments are provided so that this disclosure will be thorough and complete, and will fully convey the scope of the invention to those skilled in the art. The same reference numbers indicate the same components throughout the specification. In the attached figures, the thickness of layers and regions is exaggerated for clarity.

Unless defined otherwise, all technical and scientific terms used herein have the same meaning as commonly understood by one of ordinary skill in the art to which this invention belongs. It is noted that the use of any and all examples, or exemplary terms provided herein is intended merely to better illuminate the invention and is not a limitation on the scope of the invention unless otherwise specified. Further, unless defined otherwise, all terms defined in generally used dictionaries may not be overly interpreted.

Hereinafter, the present invention will be described in detail with reference to the attached drawings.

Figure 1:
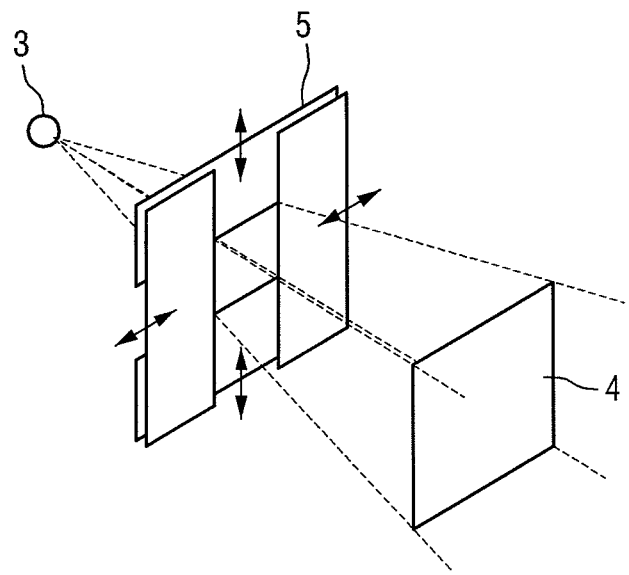
FIG. 1 is a diagram illustrating a conventional radiography device.
Figure 2:
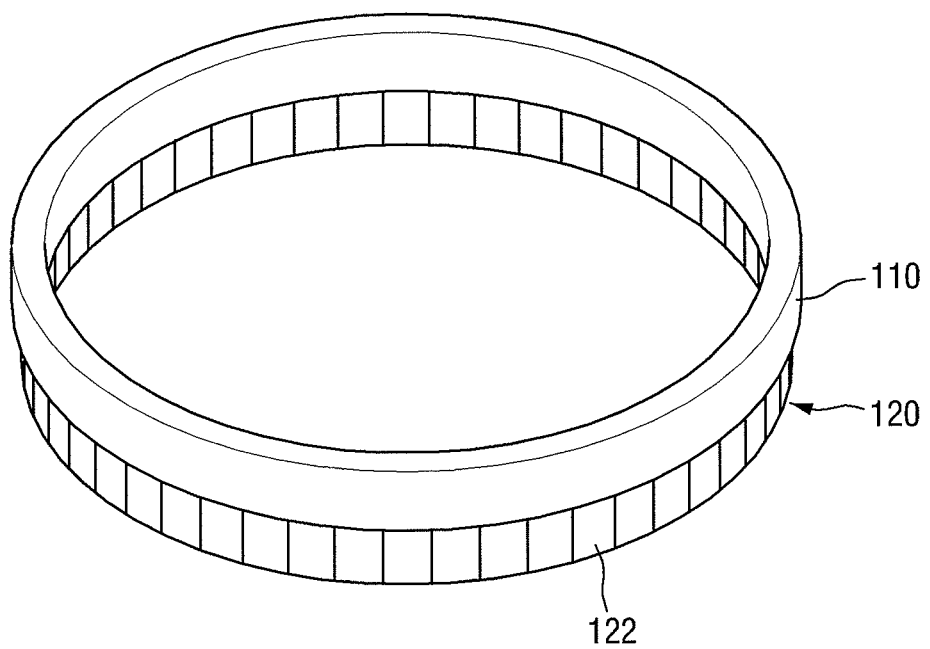
FIG. 2 is a diagram illustrating a collimator according to an embodiment of the present invention.
Figure 3:
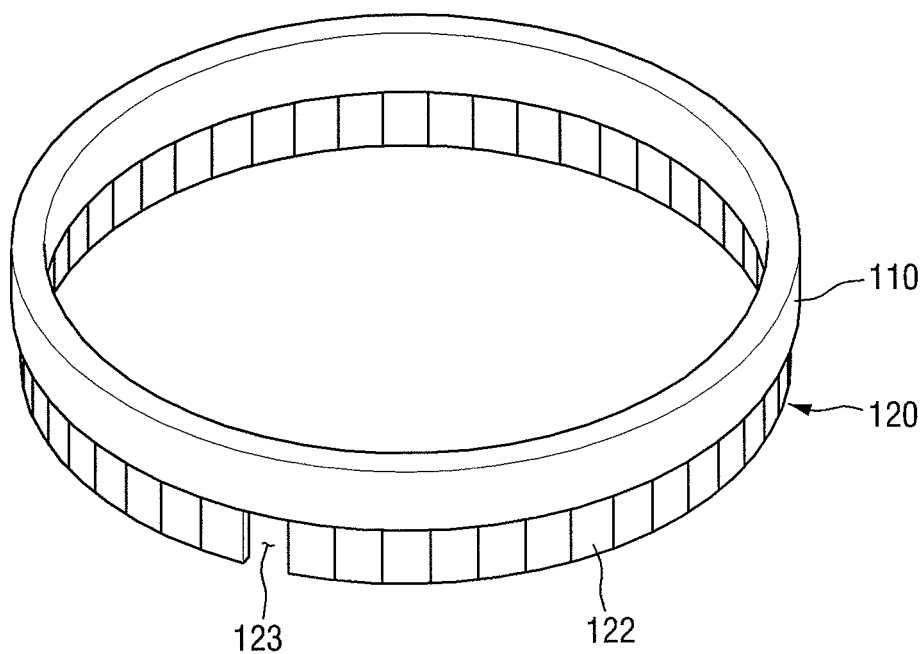
FIG. 3 is a diagram illustrating the collimator of FIG. 1 having one unit piece open.

FIG. 2 is a diagram illustrating a collimator 100 according to an embodiment of the present invention. FIG. 3 is a diagram illustrating the collimator 100 of FIG. 1 having one unit piece 122 open.

Referring to FIGS. 2 and 3, the collimator 100 according to the current embodiment sets a radiation irradiation range. To this end, the collimator 100 consists of a shielding portion 110 which blocks radiation and a block portion 120 which includes a plurality of unit pieces 122 opened or closed to selectively transmit the radiation. Each of the unit pieces 122 can be opened or closed and is inserted into the shielding portion 110 to create a space through which radiation can pass.

The shielding portion 110 is made of a radiation-absorbing material such as lead or tungsten to limit the direction and diffusion of radiation. The shielding portion 110 may also be made of other radiation-absorbing materials as will be obvious to those of ordinary skill in the art.

In addition, the shielding portion 110 may be shaped like a circular ring. The ring-shaped shielding portion 110 separates the inside and outside of the collimator 100 to block radiation.

The block portion 120 includes a plurality of unit pieces 122, and each of the unit pieces 122 may move upward or downward. In particular, each of the unit pieces 122 may be slidably inserted into the shielding portion 110, and radiation may be irradiated through a space 123 created by the insertion of each of the unit pieces 122 into the shielding portion 110. Like the shielding portion 110, the block portion 120 is made of a radiation-absorbing material such as lead or tungsten to limit the direction and diffusion of radiation. The block portion 120 may also be made of other radiation-absorbing materials as will be obvious to those of ordinary skill in the art.

In addition, the block portion 120 may be shaped like a circular ring. The ring-shaped block portion 120 separates the inside and outside of the collimator 100. Radiation is transmitted through the space 123 created by the insertion of a unit piece 122 into the shielding portion 110 and is blocked by the other unit pieces 122.

The block portion 120 may include 1,000 or more unit pieces 122. Considering that currently commercialized computed tomography (CT) obtains projection data using a maximum of 1,000 views, 1,000 or more unit pieces 122 may be installed in the block portion 120 to obtain projection views. More preferably, approximately 2,000 unit pieces 122 may be installed to increase the degree of freedom for the number of views. The number of the unit pieces 122 can be freely changed as desired.

In FIG. 3, only one unit piece 122 is inserted into the shielding portion 110. However, a number of unit pieces 122 can also be inserted simultaneously into the shielding portion 110 as will be obvious to those of ordinary skill in the art. For example, two or more adjacent unit pieces 122 in the block portion 120 may be inserted simultaneously into the shielding portion 110 such that radiation can transmit through a space created by the insertion of the unit pieces 122 into the shielding portion 110.

Figure 4A:
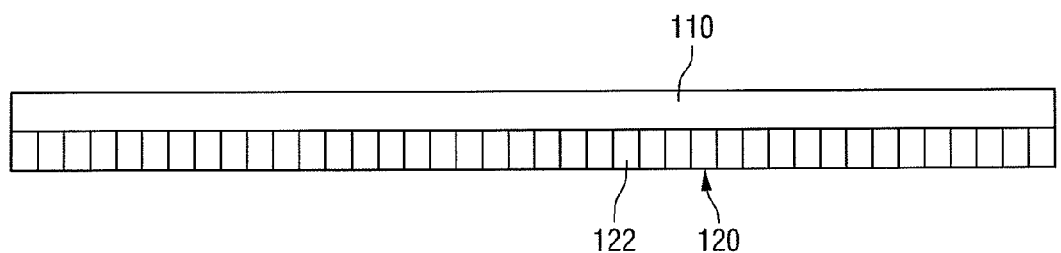
FIG. 4A is a diagram illustrating the collimator of FIG. 2 that has been spread out.
Figure 4B:
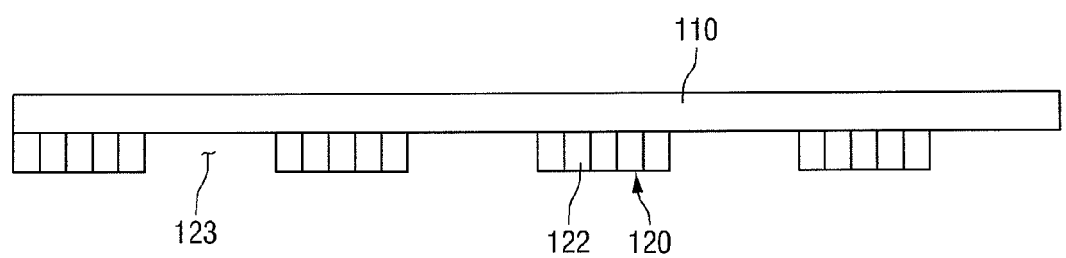
FIGS. 4B and 4C are diagrams illustrating embodiments of opening unit pieces of the collimator of FIG. 4A.
Figure 4C:
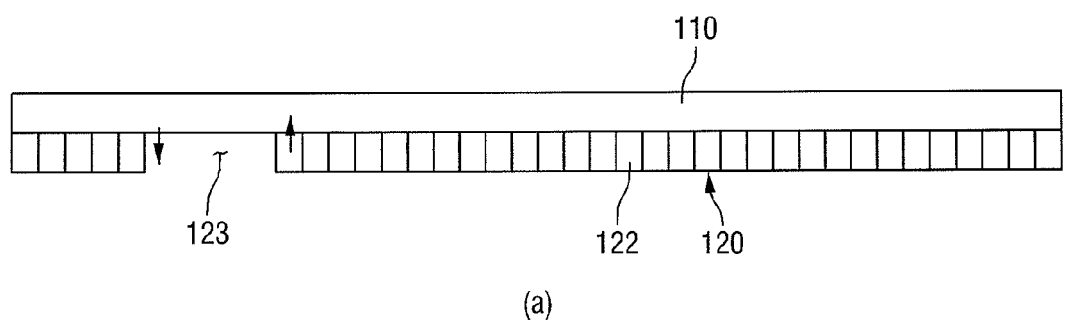
Figure 4C:
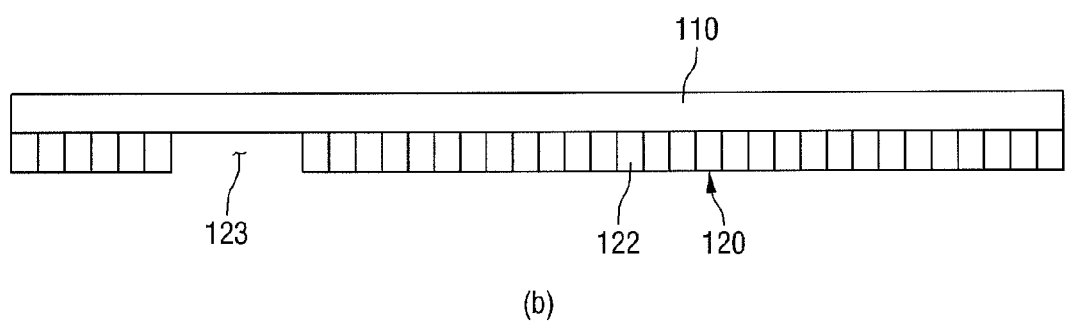

FIG. 4A is a diagram illustrating the collimator 100 of FIG. 2 that has been spread out. FIGS. 4B and 4C are diagrams illustrating embodiments of opening the unit pieces 122 of the collimator 100 of FIG. 4A.

As described above, the collimator 100 consisting of the shielding portion 110 and the block portion 120 including the unit pieces 122 may selectively transmit radiation. Referring to FIG. 4A, the collimator 100 may block radiation by not inserting the unit pieces 122 of the block portion 120 into the shielding portion 110 or transmit the radiation by inserting the unit pieces 122 of the block portion 120 into the shielding portion 110.

Here, referring to FIG. 4B, an image may be obtained using a radiation device (not shown) by inserting, in advance, a plurality of unit pieces 122 into the shielding portion 110 at regular intervals. Alternatively, referring to FIG. 4C, an image may be obtained by sequentially inserting the unit pieces 122 into the shielding portion 110 according to the movement of the radiation device (not shown) and sequentially returning the unit pieces 122 which have previously been inserted into the shielding portion 110 to their original locations. That is, the unit pieces 122 may be inserted into the shielding portion 110 regardless of the movement of the radiation device to create a space 123 through which radiation can transmit or may be inserted into the shielding portion 110 in accordance with the movement of the radiation device. The unit pieces 122 can also be inserted into the shielding portion 110 in various other ways as will be obvious to those of ordinary skill in the art.

If the collimator 100 consisting simply of the shielding portion 110 and the block portion 120 including the unit pieces 122 is installed in a gantry structured as a conventional rotatable radiation device, it is possible to overcome a technical challenge of adjusting the power of a device in the environment of the gantry rotating at high speed. Accordingly, the number of projection views and the amount of radiation to which a patient is exposed can be reduced. Conversely, the collimator 100 consisting simply of the shielding portion 110 and the block portion 120 including the unit pieces 122 may be rotatably installed in a fixed radiation device, thereby reducing the number of projection views and the amount of radiation to which a patient is exposed.

Figure 5:
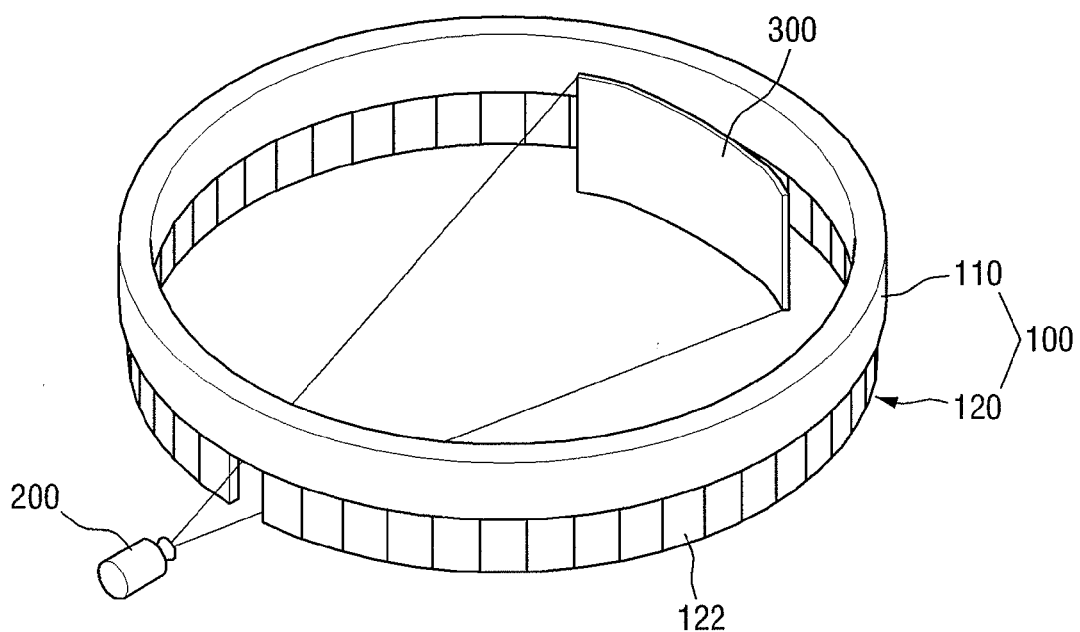
FIG. 5 is a diagram illustrating an inspecting system using a collimator according to an embodiment of the present invention.
Figure 6:
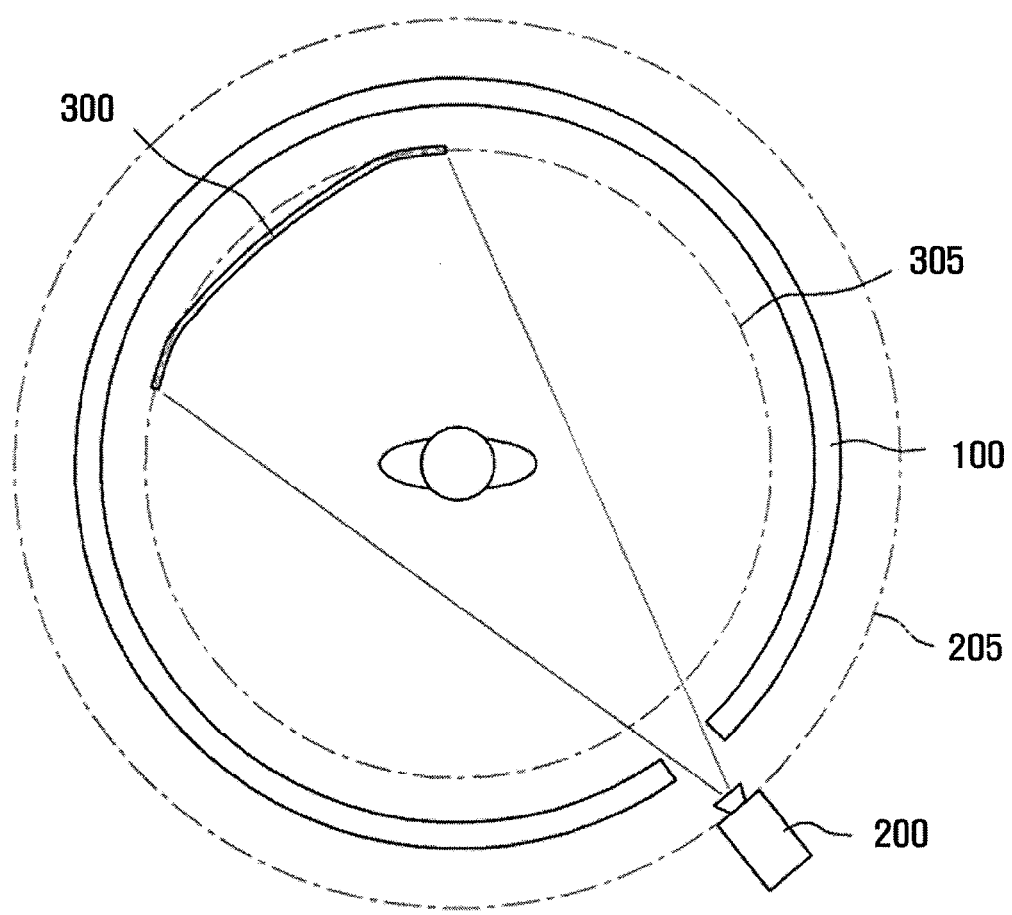
FIG. 6 is a diagram of the inspecting system of FIG. 5 viewed from above.

FIG. 5 is a diagram illustrating an inspecting system 10 using a collimator 100 according to an embodiment of the present invention. FIG. 6 is a diagram of the inspecting system 10 of FIG. 5 viewed from above.

Referring to FIGS. 5 and 6, the inspecting system 10 using the collimator 100 according to the current embodiment includes the collimator 100, a detector 300 located inside the collimator 100, and a radiation source 200 located outside the collimator 100. Specifically, the inspecting system 10 includes the radiation source 200 which irradiates radiation toward the collimator 100 as it rotates, the detector 300 which detects radiation that transmits through the collimator 100 as it rotates, and the ring-shaped collimator 100 which selectively transmits radiation irradiated from the radiation source 200 toward the detector 300.

The radiation source 200 irradiates radiation, and the detector 300 detects the radiation. The radiation source 200 and the detector 300 form a rotatable gantry structure, and the collimator 100 is placed between the radiation source 200 and the detector 300.

To selectively transmit radiation, the collimator 100 may include a shielding portion 110 which blocks radiation and a block portion 120 which includes a plurality of unit pieces 122 slidably inserted into the shielding portion 110 to transmit radiation. As described above, the shielding portion 110 and the block portion 120 are made of a radiation-blocking material, and 1,000 or more unit pieces 122 are included in the block portion 120. Since the shielding portion 110 and the block portion 120 have been described above in detail, a description thereof will be omitted.

In FIG. 6, the radiation source 200 and the detector 300 move along an outer trajectory 205 and an inner trajectory 305, respectively. As the radiation source 200 and the detector 300 move along their respective trajectories 205 and 305, the unit pieces 122 of the collimator 100 are slid into the shielding portion 110, thereby forming a space 123. Accordingly, radiation irradiated from the radiation source 200 is allowed to travel toward the detector 300. Here, the beam width of the radiation may be adjusted by appropriately controlling whether the unit pieces 122 will be inserted into the shielding portion 110 and the number of unit pieces 122 that are inserted into the shielding portion 110. For example, if all of the unit pieces 122 are inserted into the shielding portion 110, the inspecting system 10 may be put in a conventional imaging mode. Alternatively, after every ten unit pieces 122 are set as a basic group, if three unit pieces 122 from each basic group are inserted into the shielding portion 110, the inspecting system 10 can take an image in a sampling mode. Here, the number of unit pieces 122 in the sampling mode can be appropriately adjusted by an operator of the inspecting system 10.

Figure 7:
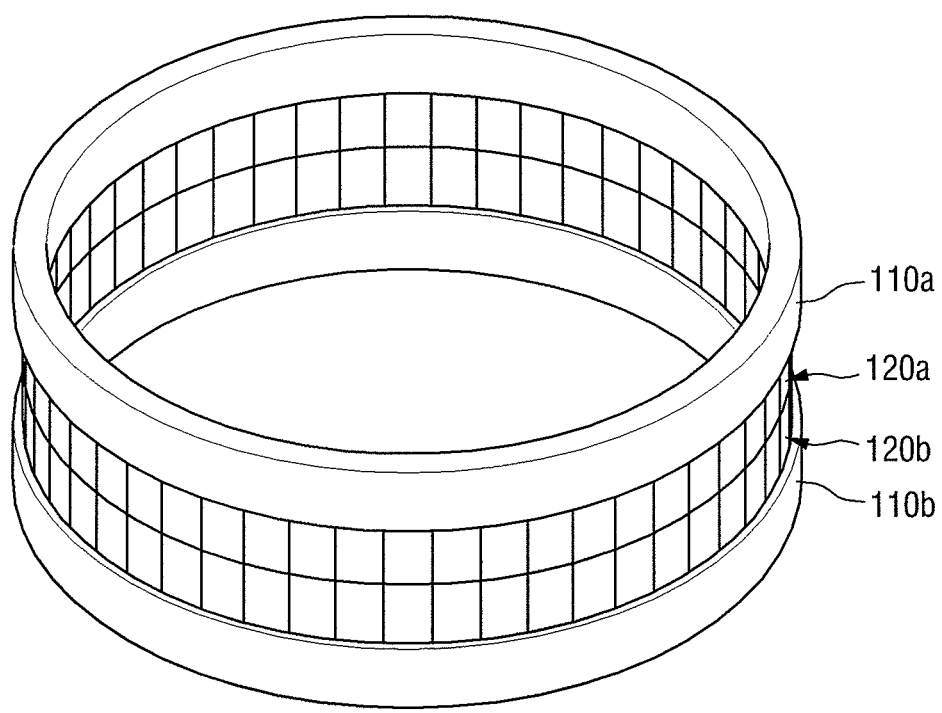
FIG. 7 is a diagram illustrating another embodiment of the collimator of the inspecting system of FIG. 5.
Figure 8A:
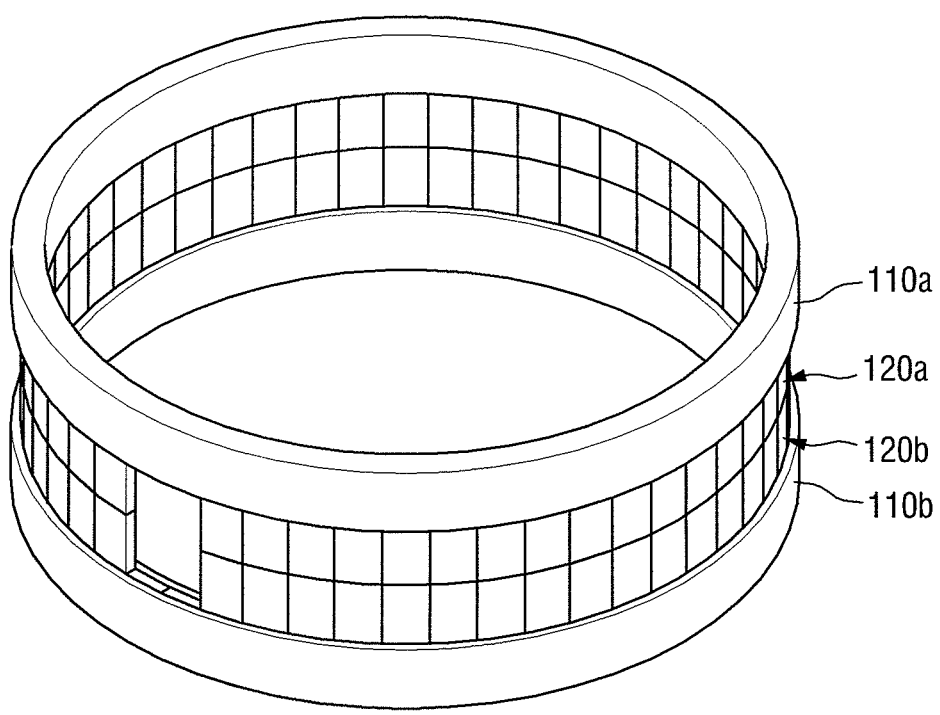
FIGS. 8A through 8C are diagrams illustrating embodiments of opening unit pieces of a collimator of FIG. 7.
Figure 8B:
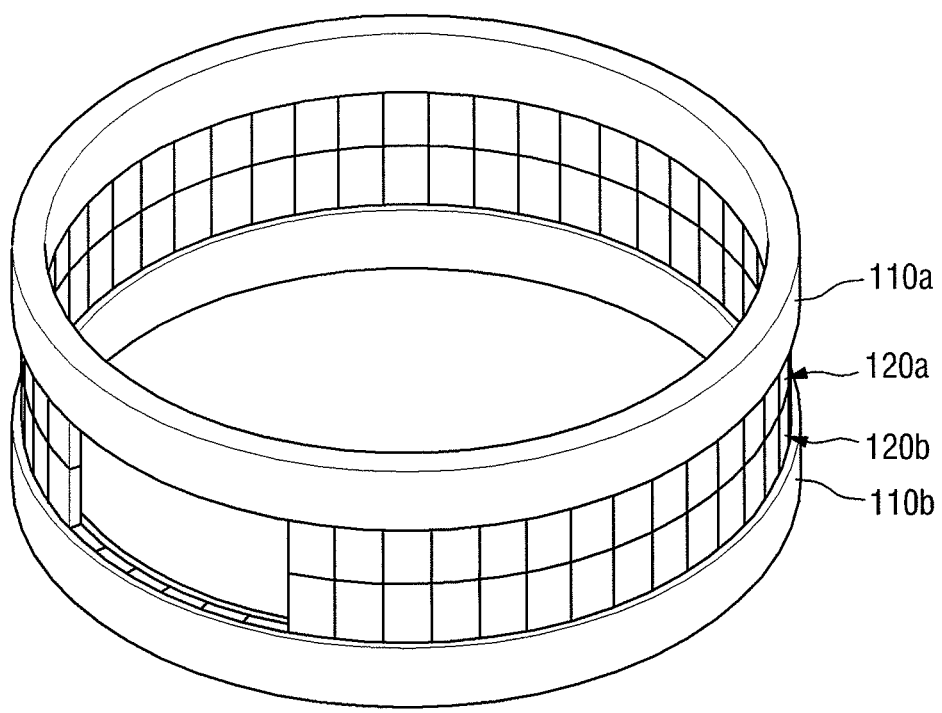
Figure 8C:
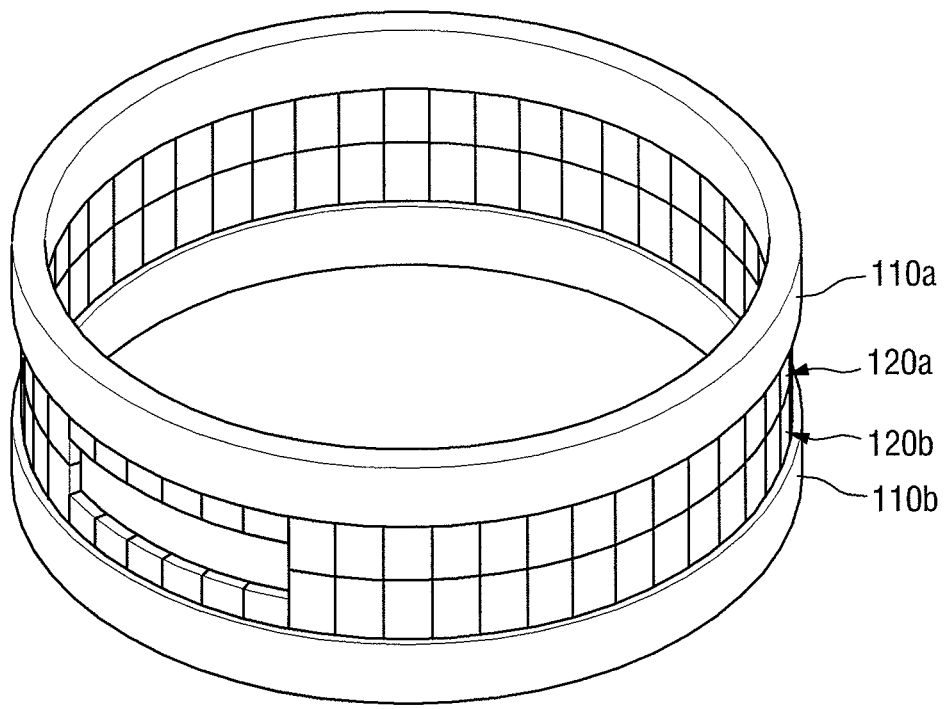

FIG. 7 is a diagram illustrating another embodiment of the collimator 100 of the inspecting system 10 of FIG. 5. FIGS. 8A through 8C are diagrams illustrating embodiments of opening unit pieces 122 of a collimator 100 of FIG. 7.

As described above, the collimator 100 may consist of a shielding portion 110 and a block portion 120. The shielding portion 110 and the block portion 120 may be placed symmetrical to each other.

Specifically, referring to FIG. 7, the shielding portion 110 may include an upper shielding portion 110a and a lower shielding portion 110b, and the block portion 120 may include an upper block portion 120a which is slidably inserted into the upper shielding portion 110a and a lower block portion 120b which is slidably inserted into the lower shielding portion 110b. Since the block portion 120 includes the upper and lower block portions 120a and 120b placed symmetrical to each other, a beam width in a z-axis plane direction can be adjusted. Here, the z axis denotes a direction in which a patient is moved while being scanned by a radiation irradiator (e.g., CT).

In FIG. 8A, unit pieces 122 of the upper block portion 120a and the lower block portion 120b may be inserted into the upper shielding portion 110a and the lower shielding portion 110b to create a space through which radiation can transmit. Further, in FIG. 8B, more unit pieces 122 of the upper block portion 120a and the lower block portion 120b than those in FIG. 8A may be inserted into the upper shielding portion 110a and the lower shielding portion 110b to increase the space through which radiation can transmit. Accordingly, the beam width in an x-y axis plane direction can be adjusted.

Here, in FIG. 8C, the unit pieces 122 of the upper block portion 120a and the lower block portion 120b may be inserted not completely but partially into the shielding portion 110 to create a space through which radiation can transmit. Accordingly, the beam width in the z-axis plane direction can be adjusted.

Figure 9A:
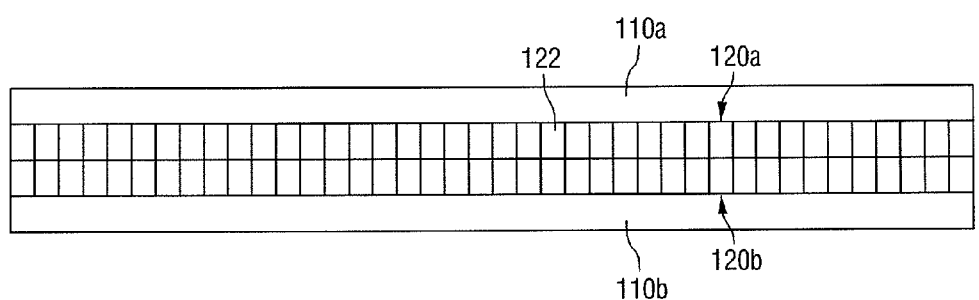
FIG. 9A is a diagram illustrating the collimator of FIG. 7 that has been spread out.
Figure 9B:
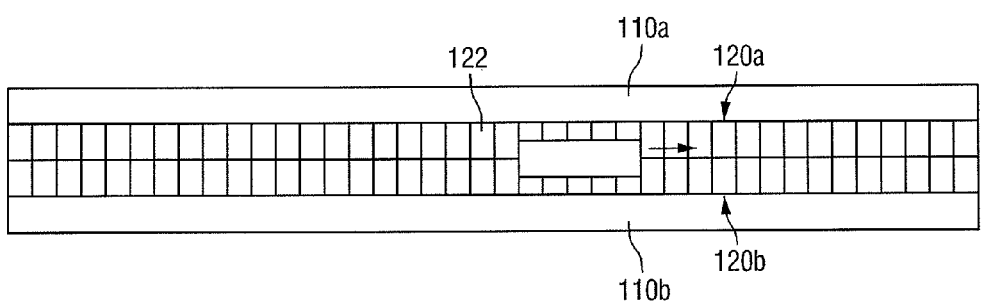
FIGS. 9B is a diagram illustrating an embodiment of opening the unit pieces of the collimator of FIG. 9A.

FIG. 9A is a diagram illustrating the collimator 100 of FIG. 7 that has been spread out. FIGS. 9B is a diagram illustrating an embodiment of opening the unit pieces 122 of the collimator 100 of FIG. 9A.

Referring to FIG. 9A, the collimator 100 may block radiation by not inserting the unit pieces 122 of the upper and lower block portions 120a and 120b into the upper and lower shielding portions 110a and 110b or transmit the radiation by inserting the unit pieces 122 of the upper and lower block portions 120a and 120b into the upper and lower shielding portions 110a and 110b. Here, an image may be obtained using the radiation source 200 and the detector 300 by inserting, in advance, a plurality of unit pieces 122 into the shielding portion 110 at regular intervals. Alternatively, an image may be obtained by sequentially inserting the unit pieces 122 into the shielding portion 110 according to the movement of the radiation source 200 and the detector 300 and sequentially returning unit pieces 122 which have previously been inserted into the shielding portion 110 to their original locations.

That is, the unit pieces 122 may be inserted into the shielding portion 110 regardless of the movement of the radiation source 200 and the detector 300 to create a space 123 through which radiation can transmit or may be inserted into the shielding portion 110 in accordance with the movement of the radiation source 200 and the detector 300. In particular, the beam width in the z-axis plane direction can be adjusted by inserting the unit pieces 122 of the upper and lower block portions 120a and 120b not completely but partially into the shielding portion 110. The unit pieces 122 can also be inserted into the shielding portion 110 in various other ways as will be obvious to those of ordinary skill in the art.

Figure 10A:
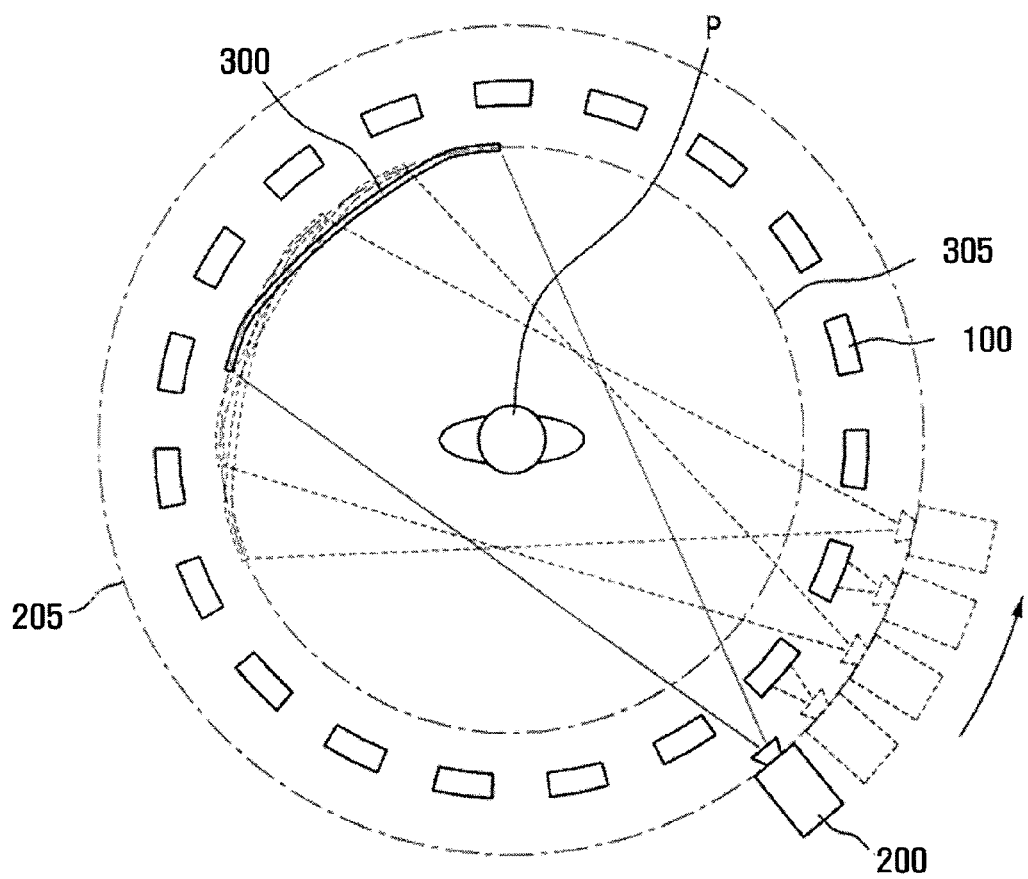
FIG. 10A is a diagram illustrating a first inspection mode of the inspecting system of FIG. 5.
Figure 10B:
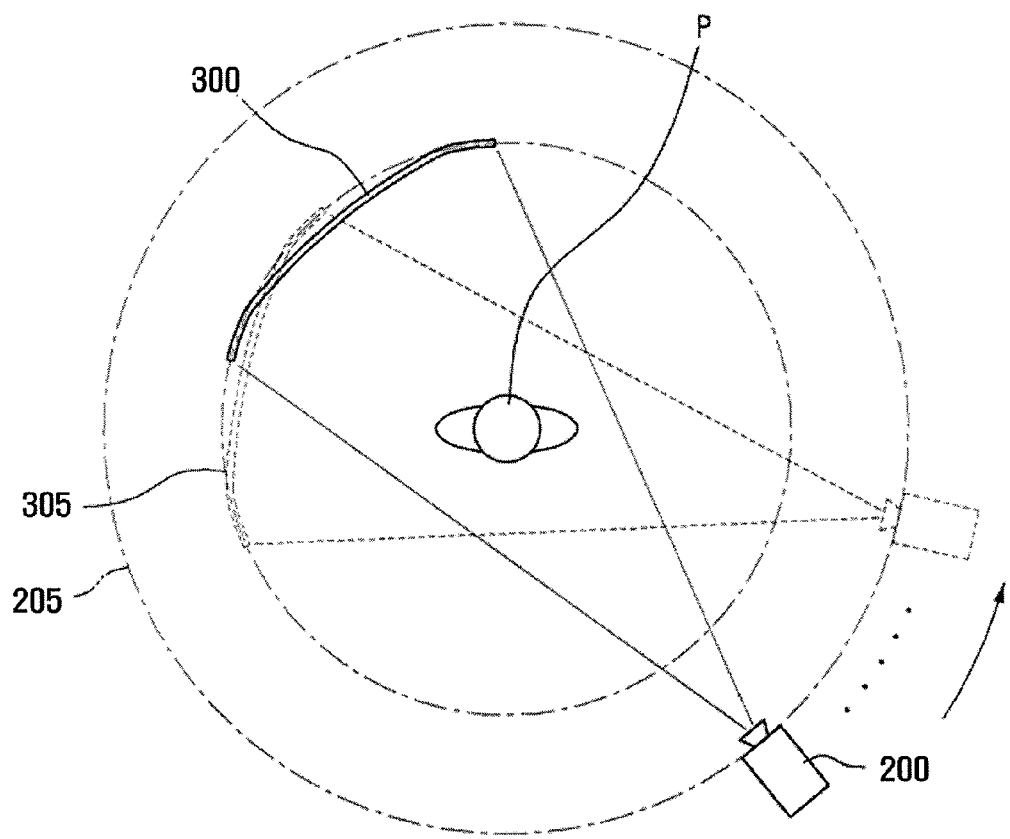
FIG. 10B is a diagram illustrating a second inspection mode of the inspecting system of FIG. 5.

FIG. 10A is a diagram illustrating a first inspection mode of the inspecting system 10 of FIG. 5. FIG. 10B is a diagram illustrating a second inspection mode of the inspecting system 10 of FIG. 5.

Referring to FIG. 10A, in the inspecting system 10, the radiation source 200 irradiates radiation through a transmission space of the collimator 100. Therefore, the amount of radiation to which a patient P is exposed is reduced. As described above, transmission spaces of the collimator 100 may be created in advance regardless of the movement of the radiation source 200 or may be created sequentially in accordance with the movement of the radiation source 200. In this way, the collimator 100 can realize a sampling mode (the first inspection mode) having a reduced number of projection views.

Referring to FIG. 10B, the radiation source 200 does not irradiate radiation through a transmission space of the collimator 100. Instead, all unit pieces 122 of the collimator 100 are open. In this case, the same effect as in a conventional imaging mode (a second inspection mode) can be obtained.

Therefore, the installation of the collimator 100 having a simple structure between the radiation source 200 and the detector 300 makes it possible to realize not only the conventional imaging mode (the second inspection mode) but also the low-dose sampling mode (the first inspection mode) in which the number of projection views can be reduced to reduce the amount of radiation exposure that the patient P will receive.

In the sampling mode (the first inspection mode), a unit piece 122 corresponding to an angle of a desired view only is opened to take an image. Since a unit piece 122 corresponding to the angle of the desired view only is opened, the number of samples can be adjusted freely. In the sampling mode (the first inspection mode), the radiation source 200 rotates at high speed while its power is always ON, and a projection view of a desired angle only is obtained using the fixed collimator 100. Therefore, it is possible to overcome a technical challenge of adjusting the power of the radiation source 200 rotating at high speed. In addition, the radiation source 200 is continuously ON, and radiation can be effectively blocked by the collimator 100 having the unit pieces 122. Therefore, it is possible to suppress blurring in an azimuthal direction, thereby improving image quality. Accordingly, a small number of projection data can be obtained, and image reconstruction based on a compressive sensing theory can be achieved. This makes it possible to realize an ultra-low-dose CT system.

According to the present invention, the number of projection views can be reduced without adjusting the power of a radiation irradiator. This can reduce the amount of radiation to which a patient is exposed.

In concluding the detailed description, those skilled in the art will appreciate that many variations and modifications can be made to the preferred embodiments without substantially departing from the principles of the present invention. Therefore, the disclosed preferred embodiments of the invention are used in a generic and descriptive sense only and not for purposes of limitation.

What is claimed is:

1. An inspecting system using a collimator, the inspecting system comprising:
   a radiation source which is located outside the collimator and irradiates radiation toward the collimator as the radiation source rotates;
   a detector which is located inside the collimator and detects radiation that transmits through the collimator as the detector rotates; and
   the collimator in the form of a ring-shaped collimator which selectively transmits radiation irradiated from the radiation source toward the detector,
   wherein the collimator comprises a shielding portion which blocks radiation and a block portion which comprises a plurality of unit pieces slidably inserted into the shielding portion to transmit radiation.

2. The inspecting system of claim 1, wherein the block portion comprises 1,000 or more unit pieces.

3. The inspecting system of claim 1, wherein the shielding portion comprises an upper shielding portion and a lower shielding portion, and the block portion comprises an upper block portion which is slidably inserted into the upper shielding portion and a lower block portion which is slidably inserted into the lower shielding portion.

* * * * *